United States Patent [19]

Berd

[11] Patent Number: 5,290,551
[45] Date of Patent: Mar. 1, 1994

[54] TREATMENT OF MELANOMA WITH A VACCINE COMPRISING IRRADIATED AUTOLOGOUS MELANOMA TUMOR CELLS CONJUGATED TO A HAPTEN

[75] Inventor: David Berd, Wyncote, Pa.

[73] Assignee: Thomas Jefferson University, Philadelphia, Pa.

[21] Appl. No.: 985,334

[22] Filed: Dec. 4, 1992

Related U.S. Application Data

[63] Continuation of Ser. No. 520,649, May 8, 1990, abandoned.

[51] Int. Cl.$^5$ .................. A61K 39/00; A61K 37/66
[52] U.S. Cl. ............................. 424/88; 424/85.2
[58] Field of Search .................... 424/88, 85.2

[56] References Cited

U.S. PATENT DOCUMENTS 4,108,983  8/1978  Wallack ......................... 424/89

OTHER PUBLICATIONS

Bystryn, J-C., *Journal of Immunology*, vol. 120 (1), pp. 96–101, (1978).
Mitchison, *Transplant. Proc.* 2:92–103 (1970).
Fujiwara et al., *J. Immunol.* 132:1571–1577 (1984a).
Flood et al., *J. Immunol.* 138:3573–3579 (1987).
Fujiwara et al., *J. Immunol.* 133:510–514 (1984b).
Berd et al., *Cancer Res.* 42:4862–4866 (1982).
Berd et al., *Cancer Res.* 44:1275–1280 (1984a).
Berd et al., *Cancer Res.* 46:2572–2577 (1986).
Berd et al., *Cancer Invest.* 6:335–347 (1988a).
Berd et al., *Cancer Res.* 44:5439–5443 (1984b).
Berd et al., *Cancer Res.* 47:3317–3321 (1987).
Berd et al., *Cancer Res.* 48:1671–1675 (1988b).
Berd et al., *Proc. Amer. Assoc. Cancer Res.* 29:408 (#1626) (1988c).
Topalian et al., *J. Clin. Oncol.* 6:839–853 (1988).
Lotze et al., *J. Biol. Response* 3:475–482 (1982).
West et al., *New Engl. J. Med.* 316:898–903 (1987).
Talmadge et al., *Cancer Res.* 47:5725–5732 (1987).
Meuer et al., *Lancet* 1:15–18 (1989).
Miller and Claman, *J. Immunol.* 117:1519–1526 (1976).

*Primary Examiner*—Margaret Parr
*Assistant Examiner*—Lisa Arthur
*Attorney, Agent, or Firm*—Woodcock Washburn Kurtz Mackiewicz & Norris

[57] ABSTRACT

The invention is a haptenized tumor vaccine for the treatment of cancer. Treatment of cancer patients with an autologous, vaccine preceded by low dose cyclophosphamide (CY) induces delayed-type hypersensitivity (DTH) to melanoma cells, and in some cases, regression of metastatic tumors. The efficiency of the process has been increased by immunizing with tumor cells conjugated to the hapten such as DNP, TNP or AED.

Additional embodiments of the vaccine include: 1) combining the vaccine with immunomodulating drugs, such as, interleukin-2 (IL2); and 2) purifying the active components of the vaccine by extracting antigens from cancer cells to produce a chemically-defined, haptenated vaccine. The treatment may also be extended to include other types of human cancer.

2 Claims, No Drawings

TREATMENT OF MELANOMA WITH A VACCINE COMPRISING IRRADIATED AUTOLOGOUS MELANOMA TUMOR CELLS CONJUGATED TO A HAPTEN

This is a continuation of application Ser. No. 520,649, filed May 8, 1990.

INTRODUCTION

The invention described herein was made in the course of work under a grant or award from an NIH Cancer Research grant.

This invention was disclosed in a Disclosure Document filed Apr. 18, 1990, which is now abandoned.

BACKGROUND OF THE INVENTION

It was theorized in the 1960's that tumor cells bear specific antigens (TSA) which are not present on normal cells and that the immune response to these antigens might enable an individual to reject a tumor. It was later suggested that the immune response to TSA could be increased by introducing new immunological determinants on cells. Mitchison, *Transplant. Proc.* 2:92–103 (1970). Such a "helper determinant", which can be a hapten, a protein, a viral coat antigen, a transplantation antigen, or a xenogenous cell antigen, could be introduced into a population of tumor cells. The cells would then be injected into an individual who would be expected to be tolerant to the growth of unmodified tumor cells. Clinically, the hope was that an immunologic reaction would occur against the helper determinants, as a consequence of which the reaction to the accompanying TSA is increased, and tumor cells which would otherwise be tolerated are destroyed. Mitchison (1970) also suggests several modes of action of the helper determinants including 1) that the unmodified cells are merely attenuated, in the sense that their growth rate is slowed down or their susceptibility to immunologic attack increased; 2) that helper determinants merely provide points of attack and so enable the modified cells to be killed by an immune response not directed against TSA; 3) that the helper determinants have an adjuvant action such as binding to an antibody or promoting localization of the cells in the right part of the body for immunization, in particular, in lymph nodes.

Fujiwara et al., *J. Immunol.* 132:1571–1577 (1984a) showed in a murine system that tumor cells conjugated with the hapten, trinitrophenyl (TNP), could induce systemic immunity against unmodified tumor cells, provided that the animals were first sensitized to the hapten in the absence of hapten-specific suppressor T cells. Spleen cells from the treated mice completely and specifically prevented the growth of tumors in untreated recipient animals. Flood et al., *J. Immunol.* 138:3573–3579 (1987) showed that mice immunized with a TNP-conjugated, ultraviolet light-induced "regressor" tumor were able to reject a TNP-conjugated "progressor" tumor that was otherwise non-immunologic. Moreover, these mice were subsequently resistant to challenge with unconjugated "progressor" tumor. In another experimental system, Fujiwara et al., *J. Immunol.* 133:510–514 (1984b) demonstrated that mice sensitized to trinitrochlorobenzene (TNCB) after cyclophosphamide (CY pretreatment could be cured of large (10 mm) tumors by in situ haptenization of tumor cells; subsequently, these animals were specifically resistant to challenge with unconjugated tumor cells.

The common denominator of these experiments is sensitization with hapten in a milieu in which suppressor cells are not induced. Spleen cells from CY-pretreated, TNCB-sensitized mice exhibited radioresistant "amplified helper function" i.e., they specifically augmented the in vitro generation of anti-TNP cytotoxicity. Moreover, once these amplified helpers had been activated by in vitro exposure to TNP-conjugated autologous lymphocytes, they were able to augment cytotoxicity to unrelated antigens as well, including tumor antigens (Fujiwara et al., 1984b). Flood et al. (1987) showed that this amplified helper activity was mediated by T cells with the phenotype Lyt-1+, Lyt-2−, L3T4+, I−J+ and suggests that these cells were contrasuppressor cells, a new class of immunoregulatory T cell.

Immunotherapy of patients with melanoma has shown that administration of CY, either high dose (1000 mg/M$^2$) or low dose (300 mg/M$^2$), three days before sensitization with the primary antigen keyhole limpet hemocyanin (KLH) markedly augments the acquisition of delayed type hypersensitivity (DTH) to that antigen (Berd et al., *Cancer Res.* 42:4862–4866 (1982); *Cancer Res.* 44:1275–1280 (1984a)). Low dose CY pretreatment allows patients with metastatic melanoma to develop DTH to autologous melanoma cells in response to injection with autologous melanoma vaccine (Berd et al., *Cancer Res.* 46:2572–2577 (1986)). The combination of low dose CY and vaccine can produce clinically important regression of metastatic tumor (Berd et al. (1986); *Cancer Invest.* 6:335–347 (1988a)). CY administration results in reduction of peripheral blood lymphocyte non-specific T suppressor function (Berd et al., *Cancer Res.* 44:5439–5443 (1984b); *Cancer Res.* 47:3317–3321 (1987)), possibly by depleting CD4+, CD45R+ suppressor inducer T cells (Berd et al., *Cancer Res.* 48:1671–1675 (1988b)). The anti-tumor effects of this immunotherapy regimen appear to be limited by the excessively long interval between the initiation of vaccine administration and the development of DTH to the tumor cells (Berd et al., *Proc. Amer. Assoc. Cancer Res.* 29:408 (#1626) (1988c)). Therefore, there remains a need to increase the therapeutic efficiency of such a vaccine to make it more immunogenic.

Most tumor immunologists now agree that getting T lymphocytes, the white cells responsible for tumor immunity, into the tumor mass is a prerequisite for tumor destruction by the immune system. Consequently, a good deal of attention has been focused on what has become known as "TIL" therapy, as pioneered by Dr. Stephen Rosenberg at NCI. Dr. Rosenberg and others have extracted from human cancer metastases the few T lymphocytes that are naturally present and greatly expanded their numbers by culturing then in vitro with Interleukin-2 (IL2), a growth factor for T lymphocytes Topalian et al., *J.Clin. Oncol.* 6:839–853 (1988). However this therapy has not been very effective because the injected T cells are limited in their ability to "home" to the tumor cite.

The ability of high concentrations of IL2 to induce lymphocytes to become non-specifically cytotoxic killer cells has been exploited therapeutically in a number of studies (Lotze et al., *J. Biol. Response* 3:475–482 (1982); West et al., *New Engl. J. Med.* 316:898–903 (1987)). However, this approach has been limited by the severe toxicity of high dose intravenous IL2. Less attention has been given to the observation that much lower concentrations of IL2 can act as an immunological adjuvant by inducing the expansion of antigen activated T cells (Talmadge et al., *Cancer Res.* 47:5725–5732 (1987); Meuer et al., *Lancet* 1:15–18 (1989)). Therefore, there remains a need to understand and attempt to exploit the use of IL2 as an immunological adjuvant.

SUMMARY OF THE INVENTION

The present invention is a haptenized tumor vaccine for the treatment of cancer. Treatment of cancer patients with a haptenized tumor vaccine, preceded by low dose cyclophosphamide (CY) has been found to induce delayed type hypersensitivity (DTH) to melanoma cells, and in some cases, regression of metastatic tumors. The efficiency of the process has been increased by immunizing with tumor cells conjugated to a hapten such as, DNP, TNP, or N-iodoacetyl-N'-(5-sulfonic 1-naphtyl) ethylene diamine (AED). Additional embodiments of the vaccine include: 1) combining the vaccine with immunomodulating drugs such as Interleukin-2; and 2) purifying the active components of the vaccine by extracting antigens from the cancer cells to produce a chemically-defined, haptenized vaccine.

DETAILED DESCRIPTION OF THE INVENTION

The invention is a form of cancer immunotherapy that involves injecting patients with a novel tumor vaccine. Patients with metastatic melanoma are immunized to the chemical dinitrophenyl (DNP) by application of dinitrofluorobenzene (DNFB) to the skin. Two weeks later, they are injected with a vaccine consisting of the patient's own cancer cells that have been irradiated and haptenized (chemically linked) to DNP. The vaccine is reinjected every 4 weeks. The drug, cyclophosphamide (CY) is administered 3 days prior to each vaccine administration to augment the immune response to the tumor cells.

The vaccine consists of $10-25 \times 10^6$ live, DNP-conjugated tumor cells suspended in 0.2 ml Hanks solution to which is added *Bacille Calmette-Guerin* (BCG) 0.1 ml. The mixture is injected intradermally into 3 contiguous sites on the upper arms or legs, excluding limbs ipsilateral to a lymph node dissection.

The vaccine is prepared as follows. Tumor masses are processed as described by Berd et al. (1986). The cells are extracted by enzymatic dissociation with collagenase and DNAse by mechanical dissociation, frozen in a controlled rate freezer, and stored in liquid nitrogen until needed. On the day that a patient is to be skin tested or treated, the cells are thawed, washed, and irradiated to 2500 R. They are washed again and then suspended in Hanks balanced salt solution without phenol red. Conjugation of the prepared melanoma cells with DNP is performed by the method of Miller and Claman, *J. Immunol.* 117:1519–1526 (1976), which involves a 30 minute incubation of tumor cells with DNFB under sterile conditions, followed by washing with sterile saline.

Other useful haptens include TNP and AED which may be chemically linked to the tumor cells.

Human cancer vaccines have been developed and tested by a number of workers. Although they can sometimes induce weak immunity to a patient's cancer, they rarely cause tumor regression. With the DNP-vaccine of the present invention, the development of inflammatory responses in metastatic tumors was surprisingly found. The tumor becomes reddened, warm and tender. Microscopically, infiltration of T lymphocytes into the tumor mass is observed. Therefore, this approach, which increases the inflammatory response and the number and capacity of lymphocytes entering the tumor, is a significant advance in the art.

It has also been found that administration of an immunomodulating drug, such as IL2, further enhances the efficacy of the present invention. In this embodiment, IL2 is given following the vaccine injection. Administration of IL2 to patients with inflammatory responses causes the T lymphocytes within the tumor mass to proliferate and become more active. The increased T cell numbers and functional capacity leads to immunological destruction of the tumors.

Recently a new preparation of IL2 has become available, which is covalently linked to polyethylene glycol (PEG). PEG-IL2 has a much longer pharmacological half-life than unmodified IL2 i.e., weekly administration results in sustained blood levels (Investigator's Brochure, Cetus Corporation). Furthermore, the toxicity of weekly administration of PEG-IL2 is mild when the weekly dose is below $1 \times 10^6$ IU/M$^2$. It was found that the administration of low dose IL2 to patients whose tumor have become infiltrated with activated T cells results in expansion of those cells and more potent anti-tumor effects. Patients with metastatic melanoma were treated using an immunotherapy regimen with the following components: 1) vaccine consisting of autologous tumor cells conjugated to DNP; 2) low dose CY pretreatment; and 3) PEG-IL2 given weekly following vaccine injection. Patients were evaluated to determine whether tumor regression had occurred, to monitor tumor inflammatory responses, and to measure DTH to autologous melanoma cells, DNFB (the form of DNP used for skin sensitization), DNP-conjugated autologous lymphocytes, diluent (Hanks solution), PPD, and recall antigens (candida, trichophyton, and mumps). Patients who are considered to be deriving benefit (clinical or immunological) from the therapy are continued in the immunotherapy regimen. Subsequent vaccines may be given without CY.

In another embodiment, a vaccine comprising chemical extracts of cancer cells conjugated to a hapten and mixed with an immunological adjuvant, such as BCG, is used. Chemical extracts of the cancer cells are prepared by protein extraction techniques from the cancer cells, followed by antigen assays to determine the most effective antigen(s) for patient treatment. The methodology for developing pharmaceuticals based on such purified active components of such a vaccine is well known in the art.

The invention is further illustrated by means of the following examples which are meant to be illustrations only and are not intended to limit the present invention to these specific embodiments.

EXAMPLE 1

Sixty-four patients were treated with metastatic melanoma using a melanoma vaccine preceded by low dose cyclophosphamide (CY) and monitored for immunological effects and anti-tumor activity. On day 0, the patients were given CY 300 mg/M$^2$IV. Three days later, they were injected intradermally with vaccine consisting of $10-25 \times 10^6$ autologous, cryopreserved, irradiated (2500 R) tumor cells mixed with BCG; the tumor cells were obtained by dissociation of metastatic masses enzymatically (collagenase and DNAse). This treatment sequence was repeated every 28 days.

The toxicity of the therapy was limited to a local inflammatory response at the injection site and mild nausea and vomiting following CY. There were 40 evaluable patients with measurable metastases; 5 had responses—4 complete and 1 partial. The median duration of response was 10 months (7-84 +months). Regression occurred not only in skin and nodal metastases, but also in lung and liver metastases. In 6 additional patients, we observed an anti-tumor response that seemed peculiar to this vaccine therapy, i.e., the regression of metastatic lesions that appeared after the immunotherapy was begun. In 3 patients this "delayed" regression occurred in two or more tumors.

Delayed-type hypersensitivity (DTH) to autologous, mechanically-dissociated melanoma cells was detectable in only 16% of patients before treatment, as compared with in 46%, 56% and 73% of patients on days 49, 161 and 217, respectively. The increases in DTH following immunotherapy were statistically significant by a non-independent t-test; day 0 vs. day 49, $p. <0.001$; day 0 vs. day 161, $p<0.001$; day 0 vs. day 217, $p=0.02$. Overall, 26/43 patients (61%) exhibited a positive DTH response (5 mm or >induration) to autologous melanoma cells at some time point. Patients also developed strong DTH to the enzymes used to prepare the tumor cell suspensions: of 24 patients tested for DTH with a mixture of collagenase and DNase (each at 1 ug/ml) after two vaccine treatments, 21 (88%) had responses >5 mm induration. Anti-tumor responses to the vaccine were strongly associated with DTH to mechanically-dissociated, autologous melanoma cells, as indicated by three observations: 1) 8/10 patients who exhibited tumor regression had positive DTH; 2) in post-surgical adjuvant patients, there was a highly significant correlation between the intensity of DTH to autologous melanoma cells and the time to recurrence of tumor ($r=0.680$, $p<0.001$); 3) nine patients who developed DTH to the autologous melanoma cells in their original vaccine ("old" tumor) developed new metastases ("new" tumor) that did not elicit DTH or elicited a much smaller response.

In three cases we were able to excise regressing tumors for histological examination; such tumors were characterized by an intense infiltration of lymphocytes. In contrast, tumors excised from these patients before immunotherapy consisted of homogeneous masses of malignant cells without significant lymphocytic infiltration.

This study shows that the use of CY allows the development of an immune response to melanoma-associated antigens in cancer-bearing patients.

EXAMPLE 2

Patients with metastatic melanoma were sensitized to DNP by topical application of dinitrochlorobenzene (DNCB) or dinitrofluorobenzene (DNFB). Two weeks later they were injected with a vaccine consisting of $10-25 \times 10^6$ autologous, irradiated melanoma cells conjugated to DNP and mixed with BCG. CY 300 mg/M²IV was given 3 days before DNCB (or DNFB) or vaccine. Of 4 patients evaluable so far, 3 have developed a striking inflammatory response in tumor masses after 2 vaccine treatments (8 weeks). Patient #1 developed erythema and swelling in the >50 large (1-3 cm) dermal metastases on her leg and lower abdomen, followed by ulceration and drainage of necrotic material, and some are beginning to regress. Biopsy showed infiltration with CD4+CD8+T lymphocytes. Patient #2 developed erythema and swelling in the skin of her lower abdomen and groin overlying large (8 cm) nodal masses. These have not yet regressed, but have changed in consistency from rockhard to fluctuant. Patient #3 exhibited moderate erythema in the skin overlying 3 subcutaneous metastases. All 3 patients have developed DTH to both DNCB and to DNP conjugated autologous lymphocytes.

EXAMPLE 3

Fifteen patients (including 3 patients from Example 2) were treated with metastatic melanoma using a novel form of immunotherapy, i.e., tumor cell vaccine conjugated to DNP. Patients were sensitized to DNP by topical application o 5% dinitrochlorobenzene. Then every 4 weeks they received cyclophosphamide 300 mg/M² followed 3 days later by injection of $10-25 \times 10^6$ autologous, irradiated melanoma cells conjugated to DNP. Most patients (92%) developed delayed-type hypersensitivity (DTH) to DNP-conjugated autologous lymphocytes or tumor cells (mean DTH=17 mm). The vaccine induced a striking inflammatory response in sc and nodal metastases in 11/15 patients, consisting of erythema, swelling, warmth, and tenderness around tumor masses, and, in one case, purulent drainage. Biopsies showed infiltration with lymphocytes, which, by immunopathological and flow cytometric analyses, were mainly CD3+, CD4−, CD8+, HLA−DR+T cells. The melanoma cells in these tissues strongly expressed ICAM-1, which serves as an adhesion molecule for T cells. Thus, DNP-vaccine seems to induce a degree of anti-melanoma immunity not seen with previously tested immunotherapy.

EXAMPLE 4

Patients with metastatic melanoma are sensitized to the hapten, 1-fluoro-2,4-dinitrobenzene (DNFB). This is the form of DNP used for skin sensitization. They are then treated with the following active immunotherapy regimen: low dose CY (obtained from Bristol Laboratories (Evansville, Ind.) which is reconstituted in sterile water and the proper dosage administered by rapid IV infusion) followed 3 days later by intradermal injection of a vaccine consisting of autologous, irradiated melanoma cells conjugated to DNP and mixed with BCG (Glaxo strain (Danish 1077) obtained from Glaxo (Greenford, England) and distributed by Quad Pharmaceuticals Inc. (Indianapolis, Ind.). The freeze-dried material is reconstituted with 1 ml sterile water; then 0.1 ml (0.8-2.6 million organisms) is drawn up, mixed with the vaccine and injected. The cyclophosphamide-vaccine sequence is repeated on days 28-31. Patients are evaluated on day 51 for tumor regression, tumor inflammatory response, and delayed-type hypersensitivity to autologous melanoma cells. They then receive three weekly injections of PEG-IL2 given as an IV bolus. PEG-IL2 was obtained from Cetus Corporation (Emeryville, Calif.). It is prepared by covalently binding PEG (6–7 Kd MW) to human recombinant IL2. The specific activity is approximately $6 \times 10^6$ IU/mg. PEG-IL2 is supplied as a sterile lyophilized product. The material is reconstituted with 1.2 ml sterile water, diluted on 50 cc 0.9% Sodium Chloride Injection, USP, and infused intravenously over 2-5 minutes. Another evaluation is performed on day 79. The entire cycle, without CY is repeated on day 84.

What is claimed:

1. A vaccine useful for the treatment of melanoma comprising irradiated autologous melanoma cells conjugated to a hapten, said hapten selected from the group consisting of dinitrophenyl, trinitrophenyl, and N-iodoacetyl-N'-5 sulfonic 1-naphtyl ethylene diamine; and mixed with an immunological adjuvant, wherein said immunological adjuvant is *Bacille Calmette-Guerin*.

2. A method for treating melanoma comprising administering cyclophosphamide followed by intradermal administration of a therapeutically effective amount of the vaccine of claim 1.

* * * * *